US012539102B2

(12) United States Patent
Soresina et al.

(10) Patent No.: US 12,539,102 B2
(45) Date of Patent: Feb. 3, 2026

(54) ULTRASOUND IMAGING SYSTEM WITH IMPROVED LOCK DEVICE

(71) Applicant: Esaote S.p.A., Genoa (IT)

(72) Inventors: Daniel Soresina, Genoa (IT); Valerio Vigo, Genoa (IT); Daniele Tedesco, Genoa (IT); Fabio Rezzonico, Como (IT)

(73) Assignee: Esaote S.p.A., Genoa (IT)

( * ) Notice: Subject to any disclaimer, the term of this patent is extended or adjusted under 35 U.S.C. 154(b) by 128 days.

(21) Appl. No.: 18/461,148

(22) Filed: Sep. 5, 2023

(65) Prior Publication Data

US 2024/0099698 A1 Mar. 28, 2024

(30) Foreign Application Priority Data

Sep. 26, 2022 (EP) .................................... 22197679

(51) Int. Cl.
*A61B 8/00* (2006.01)

(52) U.S. Cl.
CPC ............ *A61B 8/462* (2013.01); *A61B 8/4405* (2013.01)

(58) Field of Classification Search
CPC .............................. A61B 8/462; A61B 8/4405
See application file for complete search history.

(56) References Cited

U.S. PATENT DOCUMENTS

2008/0228071 A1* 9/2008 Mesaros ............ F16M 11/2092 600/437
2008/0234577 A1* 9/2008 Murkowski .............. A61B 8/00 361/825
2015/0342562 A1* 12/2015 Messina ................. H01H 9/161 248/124.1
2018/0368656 A1* 12/2018 Austin ................... A61B 1/045
(Continued)

FOREIGN PATENT DOCUMENTS

CN 105 078 507 A 11/2015
CN 207 349 729 U 5/2018
CN 109381217 A 2/2019
(Continued)

OTHER PUBLICATIONS

European Search Report and Written Opinion dated Mar. 16, 2023, which issued in the corresponding European Patent Application No. EP 22197679.8.

*Primary Examiner* — Dixomara Vargas
(74) *Attorney, Agent, or Firm* — Dickinson Wright PLLC

(57) ABSTRACT

A control panel coupled to imaging electronics in the main body housing of an ultrasonic diagnostic imaging system has
a flat panel display electrically coupled to the imaging electronics,
an articulating arm assembly to adjust viewing position of the flat panel display, and a locking mechanism to restrict articulating arm assembly motion. Articulating arm assembly has a first lower arm movably mounted to the main body or control panel, a second upper arm
(Continued)

movably connected to the first lower arm and to the flat panel display. At least one arm includes a 4-bar linkage. Locking mechanism has a protrusion and a lever with corresponding seat to engage the protrusion. The lever can pivot from a rest position in a recess, to a lock position, with the protrusion being correspondingly located to engage the seat of the lever when the lever is in the lock position.

17 Claims, 16 Drawing Sheets

(56) References Cited

U.S. PATENT DOCUMENTS

2021/0106309 A1* 4/2021 Mesaros .............. A61B 8/4405

FOREIGN PATENT DOCUMENTS

| | | | |
|---|---|---|---|
| CN | 113 958 830 | A | 1/2022 |
| CN | 216 933 270 | U | 7/2022 |
| EP | 1713396 | A1 | 10/2006 |
| WO | WO2005074806 | A1 | 8/2005 |

* cited by examiner

ULTRASOUND IMAGING SYSTEM WITH IMPROVED LOCK DEVICE

BACKGROUND

Example embodiments relate generally to the technical field of medical ultrasound imaging systems and, in particular, to lock devices, support arms thereof and ultrasound imaging systems using the same.

Cart-borne ultrasound systems are now being designed for being more ergonomically comfortable for the user to operate. Particularly, flat panel displays must be easily positioned for viewing by a user or by a patient and control panels have to be regulated in the same way for comfort use during examinations. Support devices like articulating arms are effectively used for this purpose, but during the transportation (for instance from the manufacturer to the end user, or from a hospital ward to another one) there is the need of locking or, at least, limiting the degree of freedom of the arm in order to avoid unwanted collisions and consequent damages to the devices supported.

Various systems, therefore, have been proposed for restricting relative motion between the two arms that make up an articulating arm.

CN105078507B describes a locking component comprising a locking rod, a mounting seat and an elastic body: the bottom of the locking rod is rotatably connected with the mounting seat so as to enable the locking rod to rotate up and down relative to the mounting seat, the elastic body is tightly pressed between the mounting seat and the bottom of the locking rod, the mounting seat is fixed with the lower supporting arm component, and the lock catch is arranged on the upper supporting arm component.

The restoring force of the elastic body that acts on the bottom of the locking rod, which is relevant as it allows to stabilize the lock lever in the locked/unlocked state, however, could easily cause injury to the user, because the hand that is managing the lock release easily could be in the trajectory of the rotating rod.

EP1713396A describes locking together two arms of a cart-borne ultrasound system using a catch plate that engages a spring-loaded lock plate in an articulating arm assembly having an upper arm including a 4-bar linkage which enables the flat panel display to be raised and lowered and a pneumatic piston which provides a counter-weight to the weight of the flat panel display.

The system disclosed in EP1713396A, however, poses problems of cleaning and sanification of the locking area due to the presence of an open cavity hosting the lock plate.

CN109381217B discloses a display device comprising a support arm, a first connector and a display assembly, the display assembly comprising a display and a second connector; the first end of the supporting arm is rotatably connected with the first end of the second connecting piece, the second end of the supporting arm is connected with the first end of the first connecting piece, the second end of the first connecting piece is connected with the fixed base, and the second end of the second connecting piece is rotatably connected with the display; the display or the second connecting piece is provided with a first locking piece and the first connecting piece is provided with a second locking piece; when the display assembly moves to a first position (which is the retracted position) and the display moves to a second position (rotation of 90 degree, according to one embodiment), the first locking piece and the second locking piece are locked; when the display is disengaged from the second position, the first locking member is unlocked from the second locking member.

The system in CN109381217B, however, has the drawback of requiring the display to be in a flat position for the lock to operate. This causes the footprint of the main body of the apparatus to exceed the overall dimensions of the screen to preserve the display during transportation and thus brings to an oversizing of the apparatus.

Furthermore, the system described in CN109381217B is not suitable for supporting a control panel, especially considering that the operation panel in turn carries a second arm supporting a monitor.

Thus, a need continues to exist to provide systems that allow to lock effectively, in a simpler and a safer way the articulating arm holding the display of a cart-borne ultrasound apparatus.

SUMMARY

It is thus an object of embodiments herein to provide arrangements for locking an articulating arm device of an ultrasound apparatus.

In an embodiment, an ultrasonic diagnostic imaging system, including a main body housing imaging electronics and a control panel coupled to the imaging electronics, comprises:

- a flat panel display electrically coupled to the imaging electronics;
- an articulating arm assembly to which the flat panel display is connected for adjusting the viewing position of the flat panel display, the articulating arm assembly including a first lower arm movably mounted to the main body or to the control panel and a second upper arm movably connected to the first lower arm and to the flat panel display, wherein at least one of the arms includes a 4-bar linkage, and
- a locking mechanism which acts to restrict motion of the articulating arm assembly, wherein the locking mechanism comprises a protrusion and a lever having a corresponding seat for engagement of the protrusion, the lever being hinged on one of the two arms to pivot from a rest position to a lock position, the protrusion being correspondingly located on the other arm or the control panel or a support thereof to engage the seat of the lever when the lever is in the lock position, the rest position being a non-interfering position whereby the lever is substantially contained in a recess.

In an embodiment, the recess of the locking mechanism is located in a plastic cover of the arm to which the lever is hinged and has a shape complementary to the shape of the lever so that such arm can expose an external even surface when the locking mechanism is in the rest position.

The shape of the lever may be of any type. In an embodiment it is substantially a parallelepiped with a first and a second opposing flat surfaces, wherein the first surface is adapted to contact the arm to which the lever is hinged when the lever is in rest position while the second surface is adapted to contact the protrusion or a support thereof when the lever is in lock position.

The lever may be advantageously maintained in the lock position by an attraction force acting between a first element associated to the lever, particularly to the second surface of the lever, and an element associated to the protrusion or a support thereof.

In an embodiment, the element associated to the protrusion is a metallic element, like the head of a screw, fixed to the protrusion or to a support thereof, while the first element associated to the lever is a magnet fixed to the lever or a support thereof or vice versa.

According to a variant, the element associated to the protrusion and the first element associated to the lever may be corresponding parts of a fastening device of the hook-and-loop type. Mechanical fastening can be alternative or in addition to magnetic force coupling.

In an embodiment, the lever comprises a second element, for example associated to the first surface of the lever, configured to exert a magnetic force on the metallic body of the arm to which the lever is hinged, or on a metallic element, like the head of a screw, associated to such arm, when the lever is in rest position.

The lever has typically a slit in the end portion hosting a transversal cylindrical portion acting as a pivot axis.

The lever may further comprise a prolongation of the cylindrical portion on one side of the lever ending with a gripping appendix substantially coplanar with the lever and extending in the opposite direction of the lever so that when the appendix is rotated in one direction around the pivot axis the lever rigidly rotates in the same direction.

The prolongation of the cylindrical portion may also extend on the opposite side of the lever and end with a further gripping appendix so that the lever can be indistinctly rotated acting on either side.

In an embodiment, the lever is hinged to the second arm while the protrusion is associated to the control panel or a support thereof or the lever is hinged to the first arm while the protrusion is associated to the second arm.

The protrusion may advantageously be an elongated element extending from a support block fixed, or to be fixed, to the control panel or the main body, such block having a flat surface adapted to contact the second surface of the lever when in lock position, the attraction element associated to the protrusion being located on such flat surface.

The attraction element may be the head of a screw fixing the support block to the control panel or the main body, The protrusion may also have the shape of a hook for holding the probe cable when the lever is in rest position.

Several variants are possible. For example, in an embodiment the locking device includes, on the first arm, an internal metallic structure, a mechanism, constituted in turn by a holed lever and two magnets, and a plastic cover with a specific shaped hole to receive the lever. The locking device also includes a component having a protrusion fixed on the upper portion of the control panel with a screw realized in magnetic material.

The lever has a rest position (flat along the first arm) and a work position, at about 90 degrees.

When the support device is to be fixed, the upper arm is lowered to achieve the retracted position, the lever is rotated from the rest position to the work position and the protrusion placed in the control panel engages the hole in the lever. The engagement and the keeping in the locked state are possible, first of all, thanks to the geometric interference between the draft of the protrusion and the hole placed in the lever, then they are also assisted thanks to the attraction force between the fixing screw on the component with the protrusion and the first magnet on the lever.

When the support device can return to the unlocked state, the lever is rotated from the work position onto the rest position, and the attraction force between the second magnet on the lever and the metallic structure on the first arm helps the keeping of the lever in the predetermined rest position.

In a further embodiment, the component having a protrusion is fixed on the second arm of the articulating arm, instead of on the control panel.

In an advantageous configuration with internal structures of the arms forming the articulating arm realized in non-magnetic material or with the plastic cover that cannot be holed, there is a screw in magnetic material into the recess receiving the lever in the first arm.

The articulating arm assembly can be equally used for connecting the control panel to the main body. In this case the first lower arm is to be connected to the main body while the second upper arm is to be connected to the control panel.

Two articulating arm assemblies may also be used for supporting both the flat panel display and the control panel using the same or different locking mechanisms. To such extent, in a variant, the system comprises an additional articulating arm assembly to which the control panel, or the flat panel display, is connected, the additional articulating arm assembly including an additional first lower arm movably mounted to the main body or the control panel and an additional second upper arm movably connected to the additional first lower arm and to the control panel, or the flat panel display, and an additional locking mechanism which acts to restrict motion of the additional articulating arm assembly, wherein the additional locking mechanism comprises an additional protrusion and an additional lever having a corresponding additional seat for engagement of the additional protrusion, the additional lever being hinged on one of the additional two arms to pivot from a rest position to a lock position, the additional protrusion being correspondingly located on the other additional arm or the main body or the control panel or a support thereof to engage the additional seat of the additional lever when the additional lever is in the lock position, the rest position being a non-interfering position whereby the additional lever is substantially contained in a recess.

The characteristics of the additional articulating arm assembly and related locking mechanism, if present, are the same as disclosed with reference to a single assembly.

Further improvements of the invention will form the subject of the dependent claims.

BRIEF DESCRIPTION OF THE DRAWINGS

The characteristics of example embodiments of the invention and the advantages derived therefrom will be more apparent from the following description of non-limiting embodiments, illustrated in the annexed drawings, in which.

DETAILED DESCRIPTION OF EXAMPLE EMBODIMENTS

Figure 1:
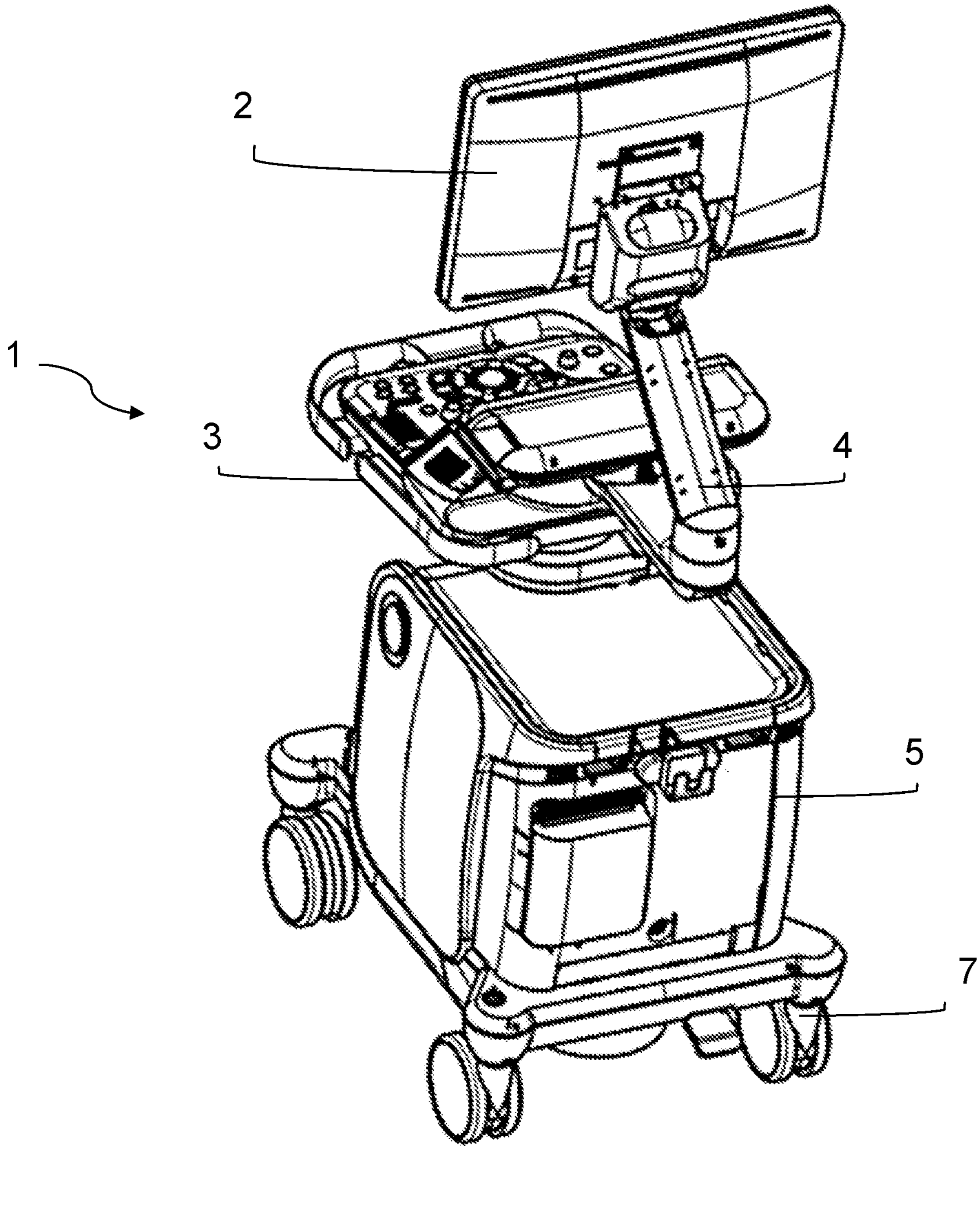
FIG. 1 shows a perspective view of an ultrasound apparatus according to an embodiment.

Referring to FIGS. 1 to 9, an ultrasound apparatus 1 includes a main body 5, a control panel 3, an articulating arm 4 and a display 2. The control panel 3 is mounted on the main body 5, in turn mounted on the wheel assembly 7. In the illustrated embodiment the articulating arm 4 is mounted on the control panel 3, and the display apparatus 2 is mounted on the upper support arm assembly 41 of the articulating arm 4 through a joint 44.

Figure 2A:
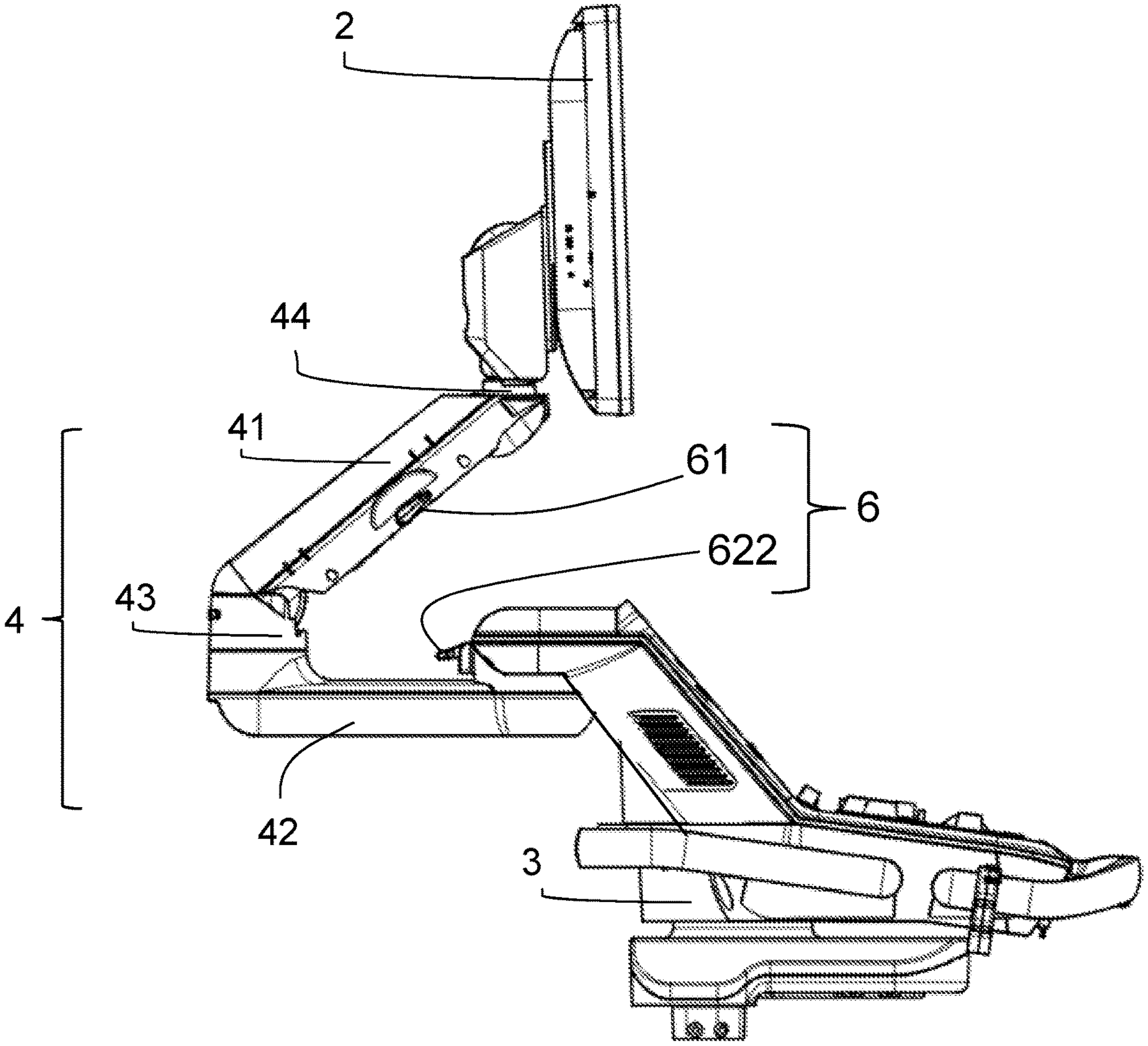
FIG. 2*a* shows an enlarged view of the upper portion of the ultrasound apparatus according to FIG. 1.
Figure 2B:
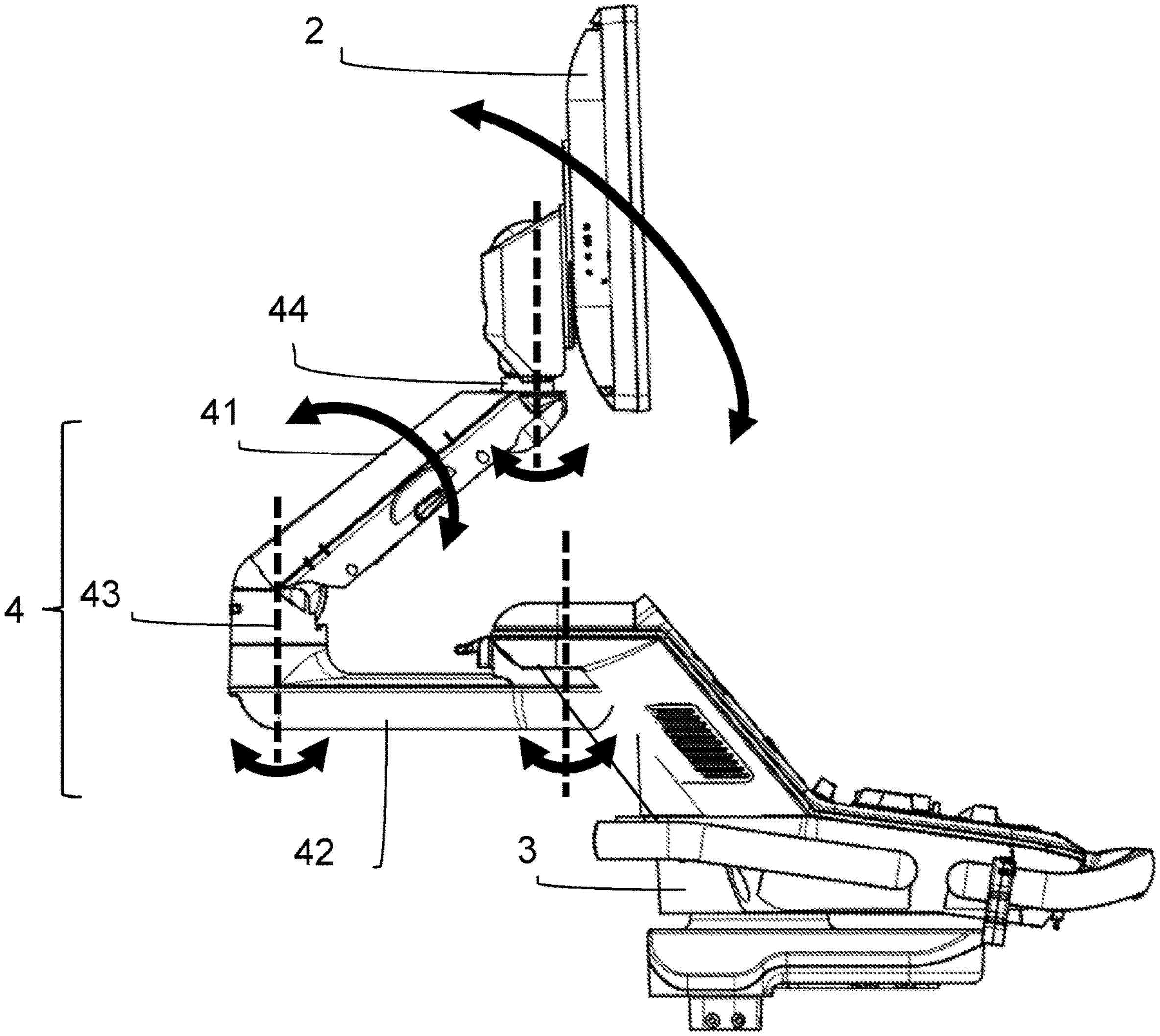
FIG. 2*b* shows the allowed movements of the articulating arm of FIG. 2*a*.

The articulating arm 4 comprises an upper arm 41, a lower arm 42 and a joint connection 43 between the two arms. The upper and lower arms (41, 42) include 4-bar linkages, for example realized by die casting, and kinematically forming a pantograph with the joint 43. Referring in particular to FIG. 2*b*, where the arrows symbolize the allowed movements and the vertical rotation axis are represented by dashed line, the lower arm 42 can rotate around the vertical axis in its end connected with the operation panel 3; while the upper arm 41 (through the joint 43) can rotate left and right in a horizontal plane and rotate up and down in a vertical plane relative to the lower arm 42. The display 2 can rotate around a vertical axis and up and down through the joint 44.

Figure 5:
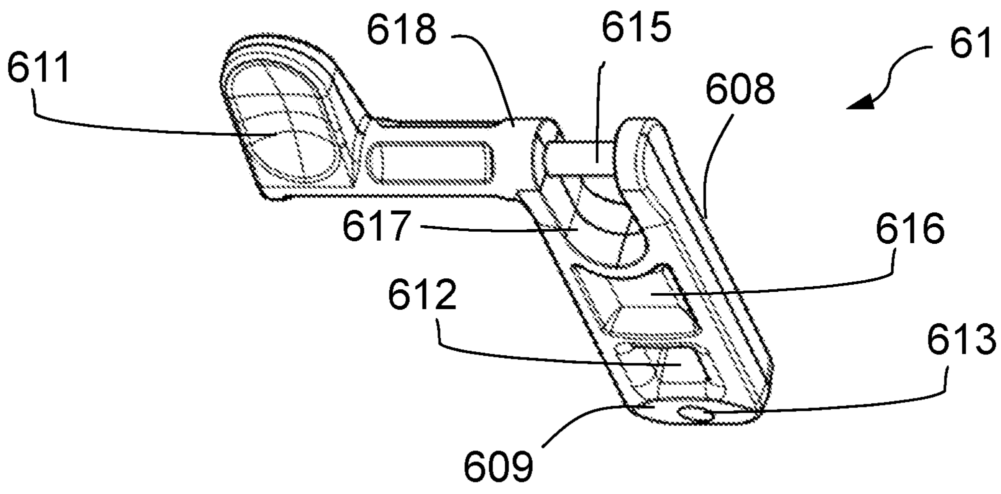
FIG. 5 is a detailed view of the lever of FIGS. 1 and 2.
Figure 6:
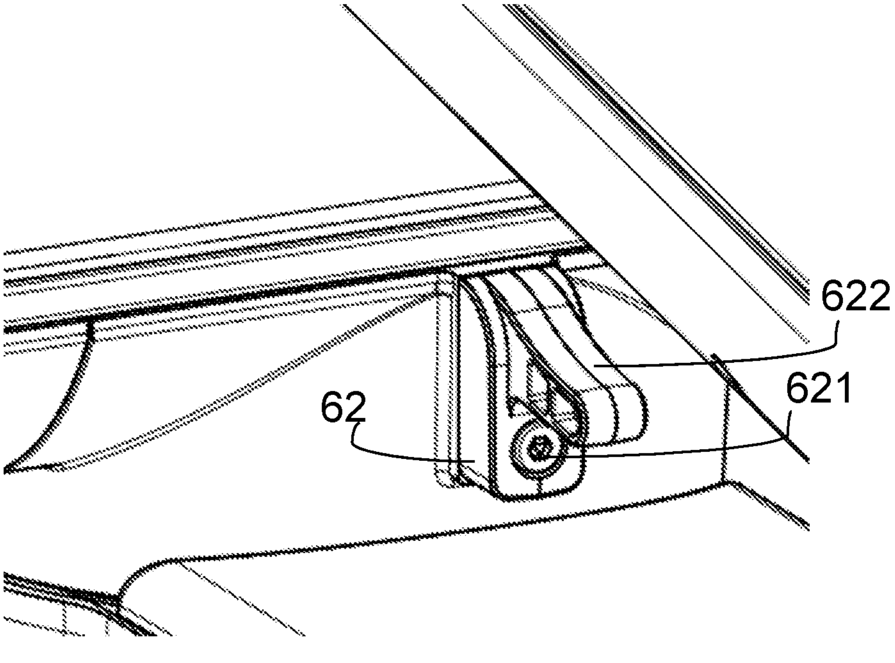
FIG. 6 shows an assembled component bearing a protrusion for engagement with the seat of the lever.
Figure 7:
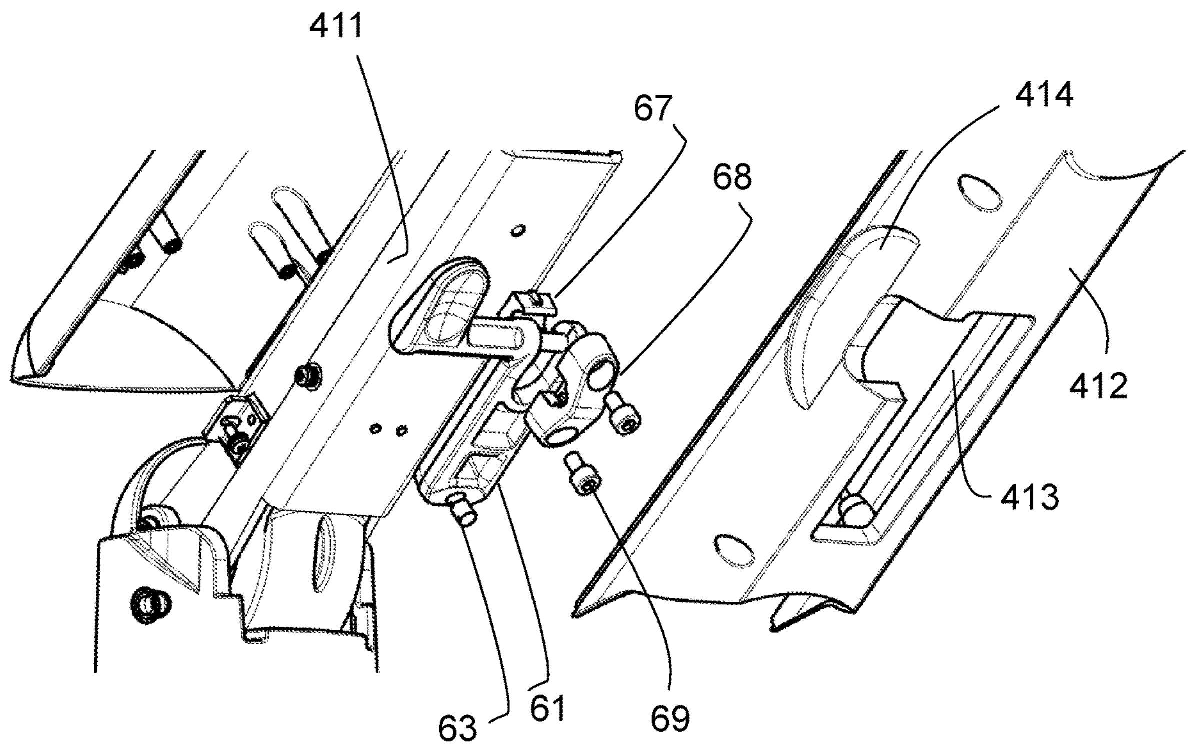
FIG. 7 shows the exploded view of the locking mechanism according to an embodiment.

The upper arm 41 comprises a mechanism including a lever 61, a plastic cover 412 facing the lower arm 42 and shaped with a first holed recess 413 to receive the lever 61 leaving exposed the internal structure 411 and, optionally, a second recess 414 that is, for example, the involute surface of the trajectory of the grip 611. This last feature makes sure that the grip 611 does not rub against the plastic cover 412 and, at the same time, that it does not stick out excessively. The lever 61 includes in a single element a grip 611, a first through hole 612, a second hole 613 and a third hole 614 on the opposite side 608. In the hole 613 is installed a magnet 63, while in the hole 614 is installed the magnet 64. It's also present a cylindrical area 615 having a lateral extension 618 bearing the grip 611. Lightening and/or mounting features 616, 617 (such as recesses and slits) on both sides can be added, carrying as second advantage a material saving. As shown in FIG. 5, the geometry of the lever is very simple and can be realized directly by moulding. Furthermore, considering levers with the same overall dimensions and material, the geometry of the lever of example embodiments of the present invention makes it be lighter than the levers of the cited prior art and this makes possible for the user to move a minor mass and make less effort. The area of connection between the lower arm and the control panel has a component 62 having a protrusion 622 fixed with a screw 621 realized in magnetic material (such as common steel) on flat surface 623. The component 62 can be realized by moulding and in this way the protrusion 622 naturally have drafts as a result of the manufacturing process.

The lever 61, the magnets 63 and 64 and the component 62 constitute the lock device 6.

The lever 61 is hinged to the fixing element 68 and its counterpart 67 and can only rotate around the axis of the cylindrical area 615. Parts 68 and 67 are fixed to the internal structure 411 through screws 69.

The lever 61 has a rest position and a work position.

Figure 3:
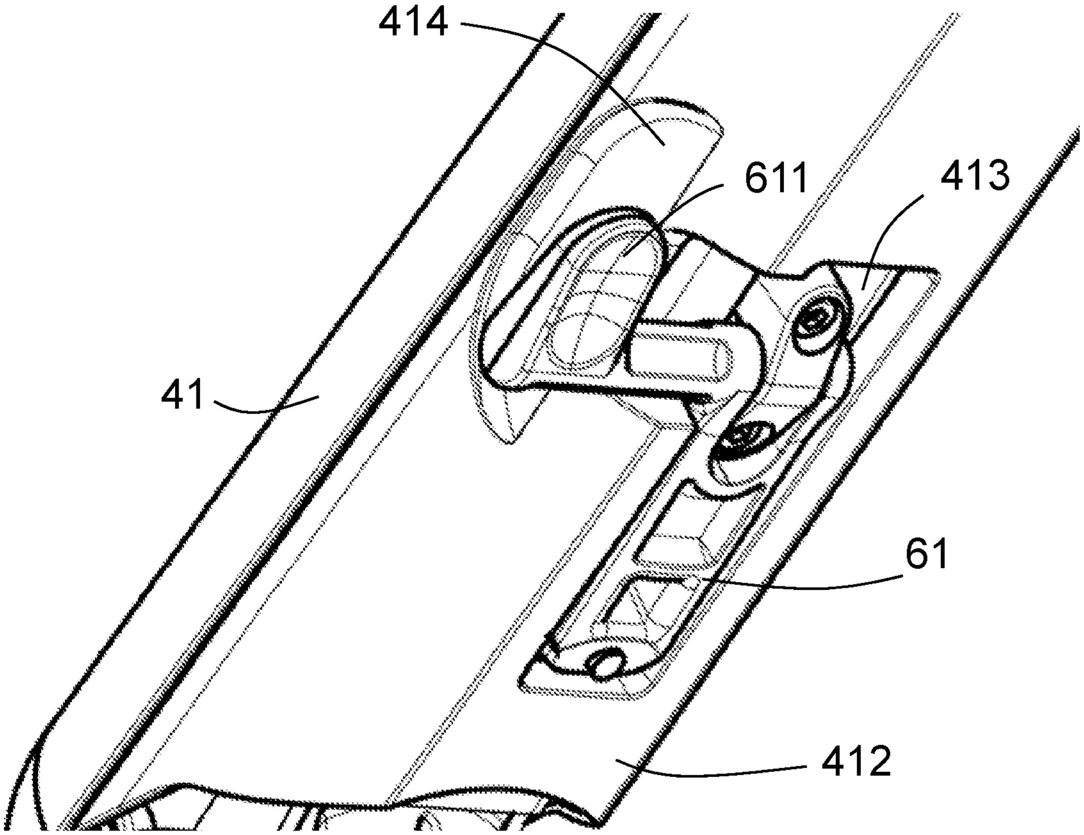
FIG. 3 shows the locking mechanism according to an embodiment with the lever in the rest position.
Figure 4:
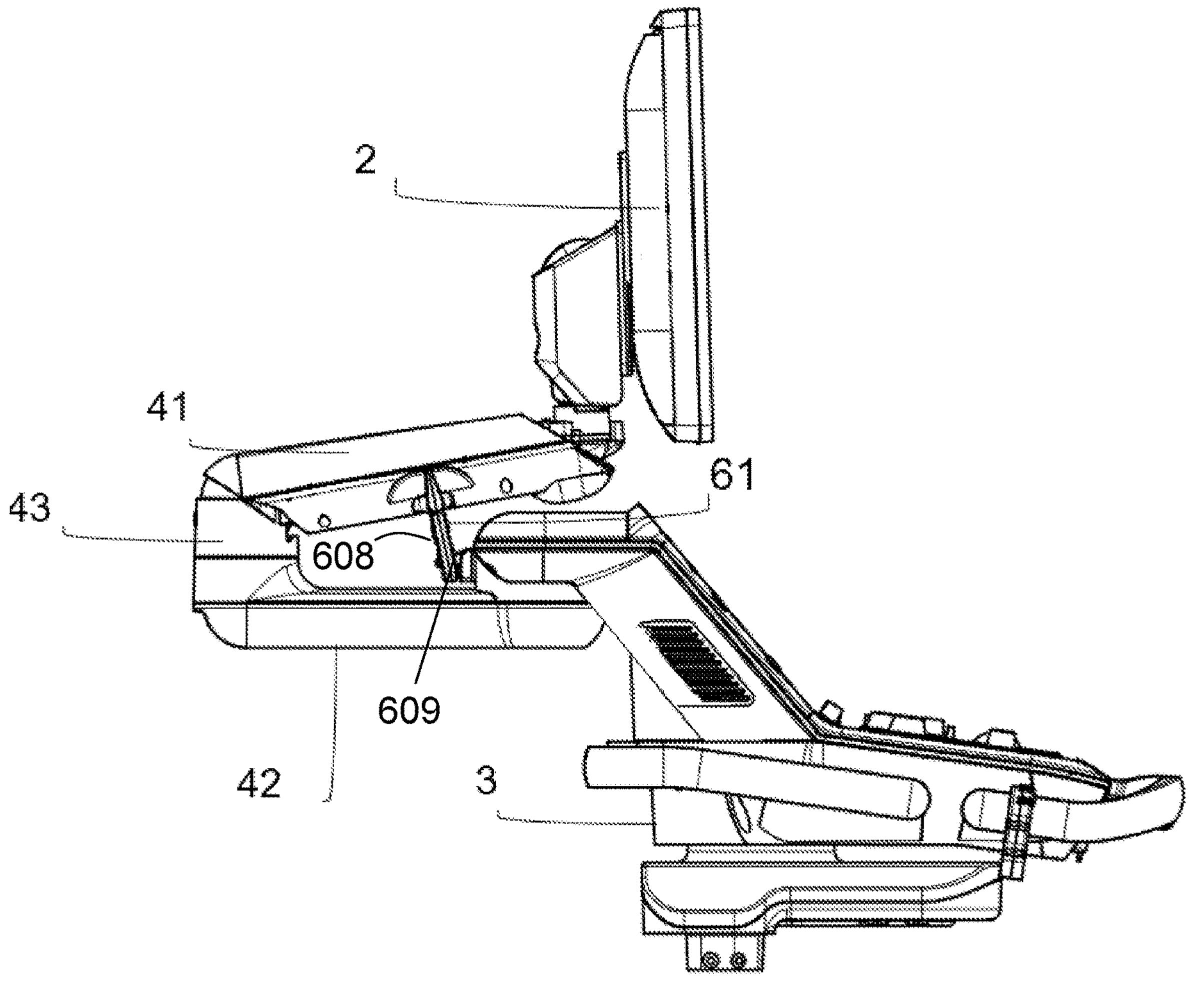
FIG. 4 shows the upper portion of the ultrasound apparatus of FIG. 1 where the lever is in the work position.

The rest position is shown in FIG. 3: The lever 61 is flat along the first arm and is received by a recess in the cover 412. The work position is shown in FIG. 4: the lever 61 is rotated of about 90 degrees from the rest position.

Figure 8:
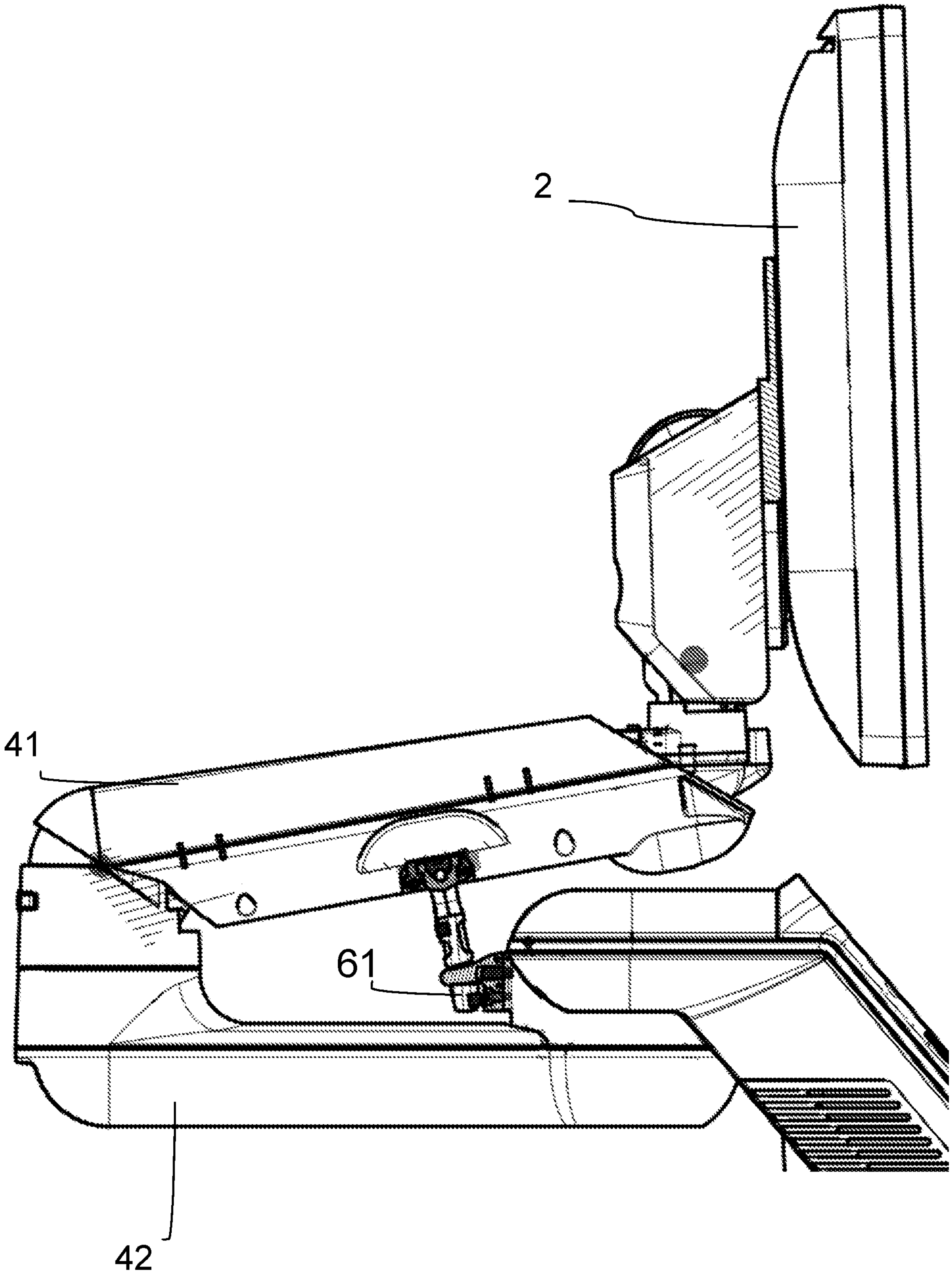
FIG. 8 shows the partial cross section of FIG. 2*a* where the lever is in the work position.
Figure 9:
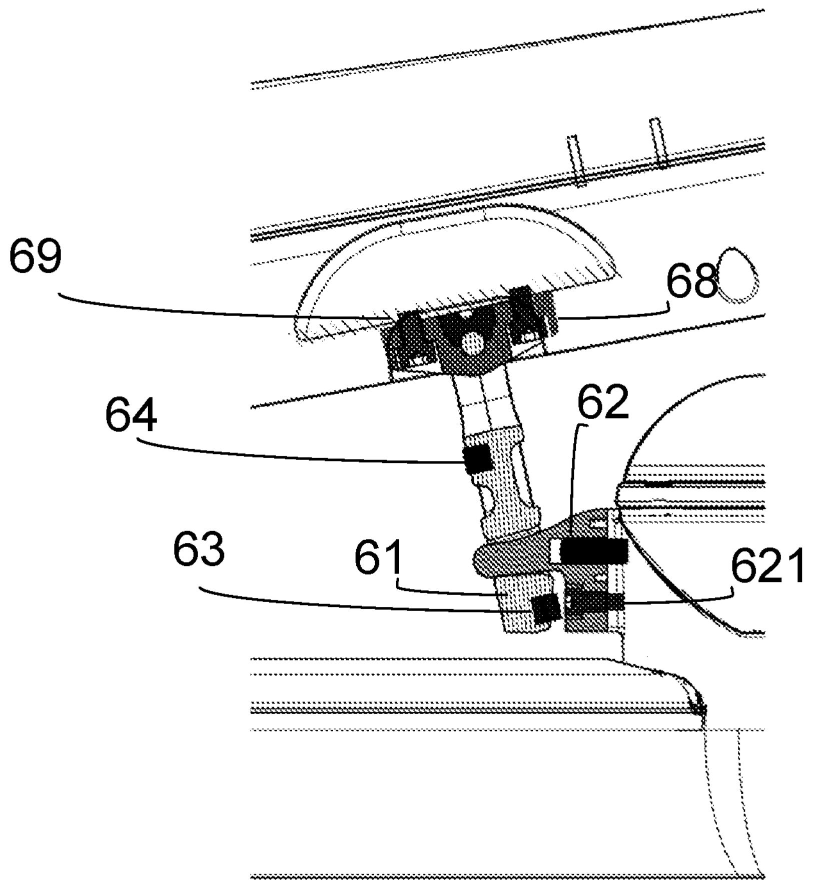
FIG. 9 is an enlarged view of the lever and the protrusion engaged according to FIG. 8.

Referring to FIGS. 8 and 9, when the support device (for instance the display 2) is to be fixed, the upper arm 41 is lowered, the lever 61 is rotated and the protrusion 622 engages the hole 612. The engagement and the keeping in the locked state are possible thanks to the geometric interference between the draft of the protrusion 622 and the hole 612 placed in the lever 61, then they are assisted thanks to the attraction force between the screw 621 and the magnet 63.

When the support device can return to the unlocked state, the lever 61 is rotated from the locked position to the rest position, and the attraction force between the magnet 64 and the internal metallic structure 411 of the arm 41 assists the keeping of the lever 61 in the predetermined rest position (e.g., flat along the upper arm 41).

Figure 10A:
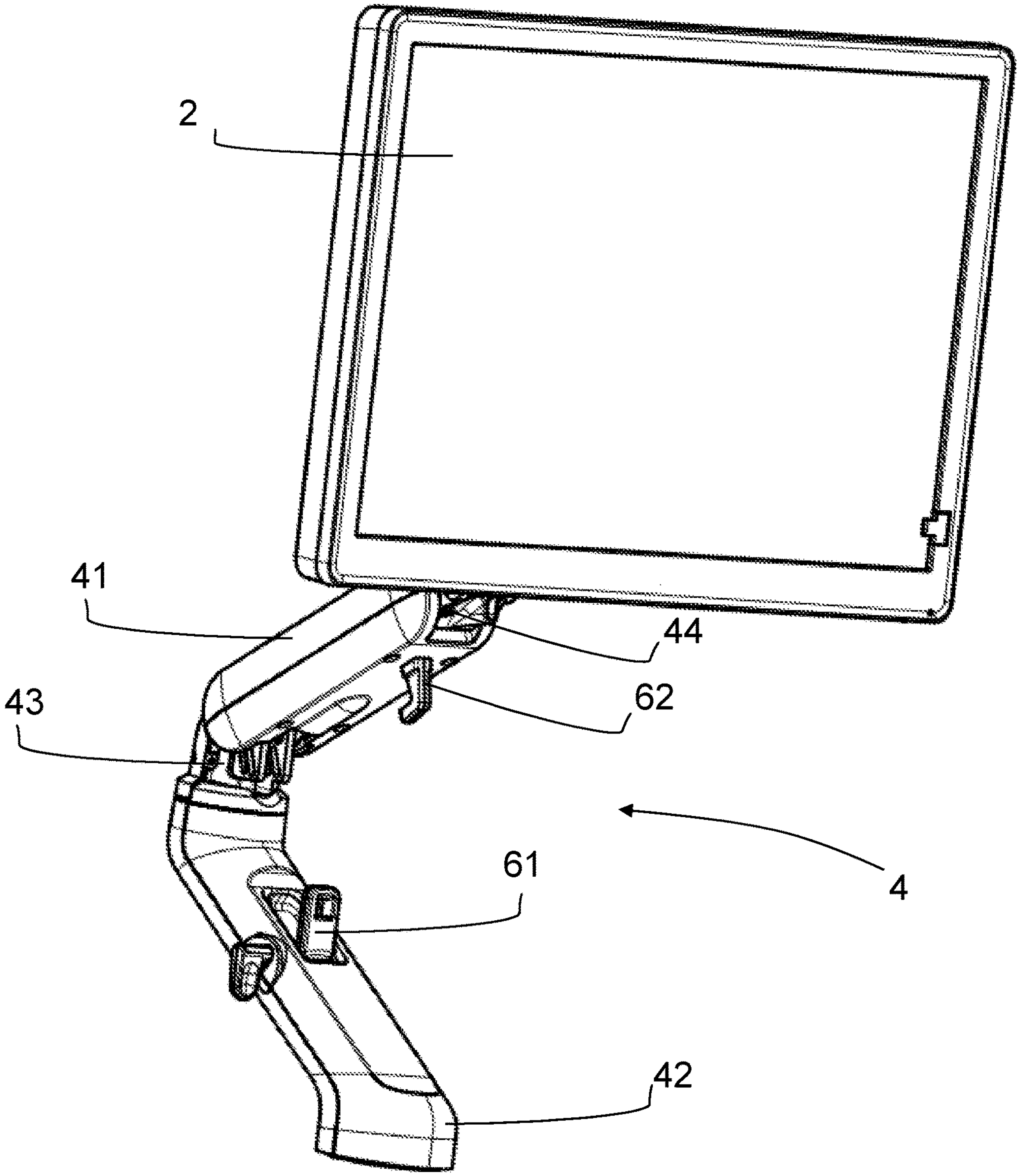
FIG. 10*a* is a perspective view of an articulating arm assembly according to another embodiment where the component having a protrusion is in the upper arm and the lever in the lower arm.
Figure 10B:
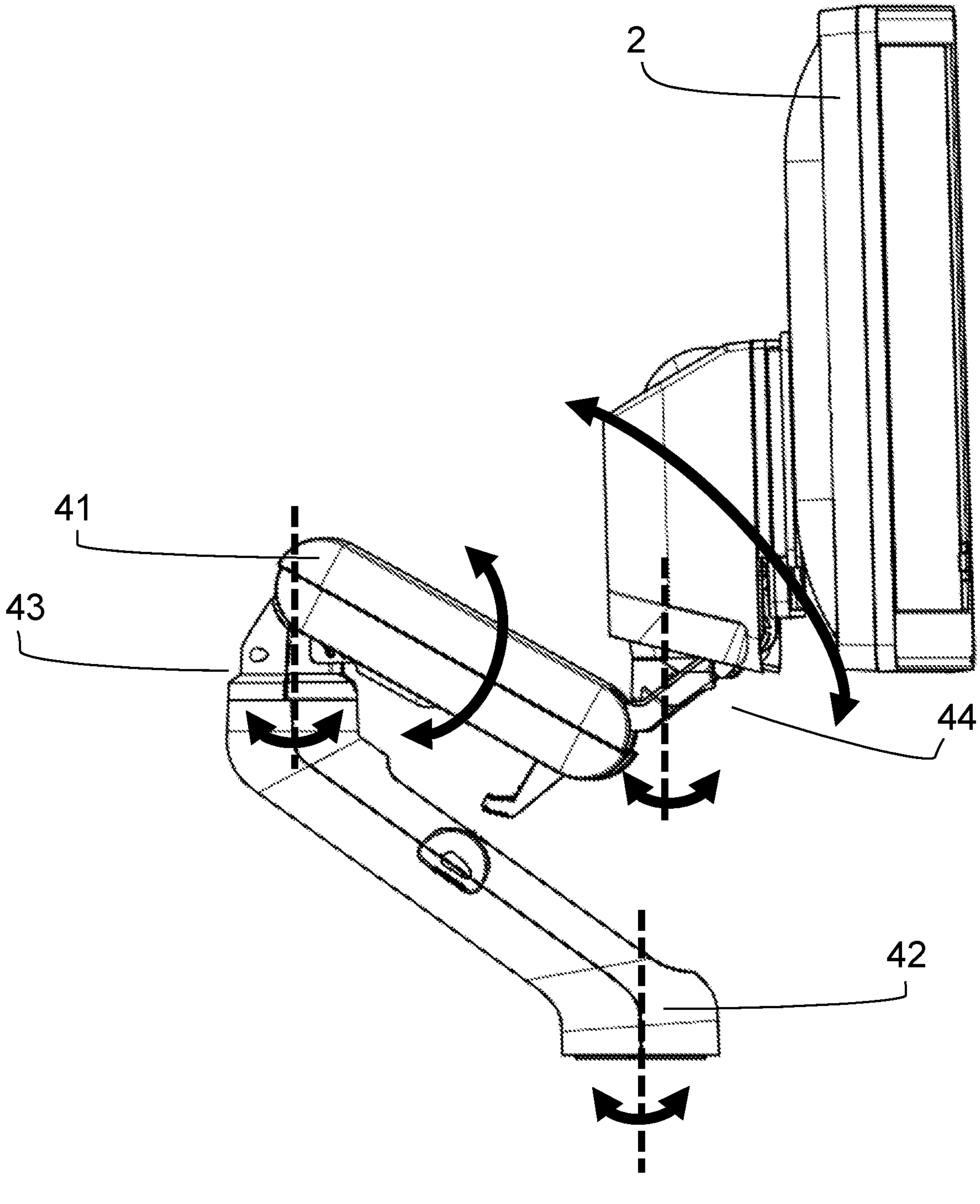
FIG. 10*b* shows the allowed movements of the articulating arm of FIG. 10*a*.
Figure 11:
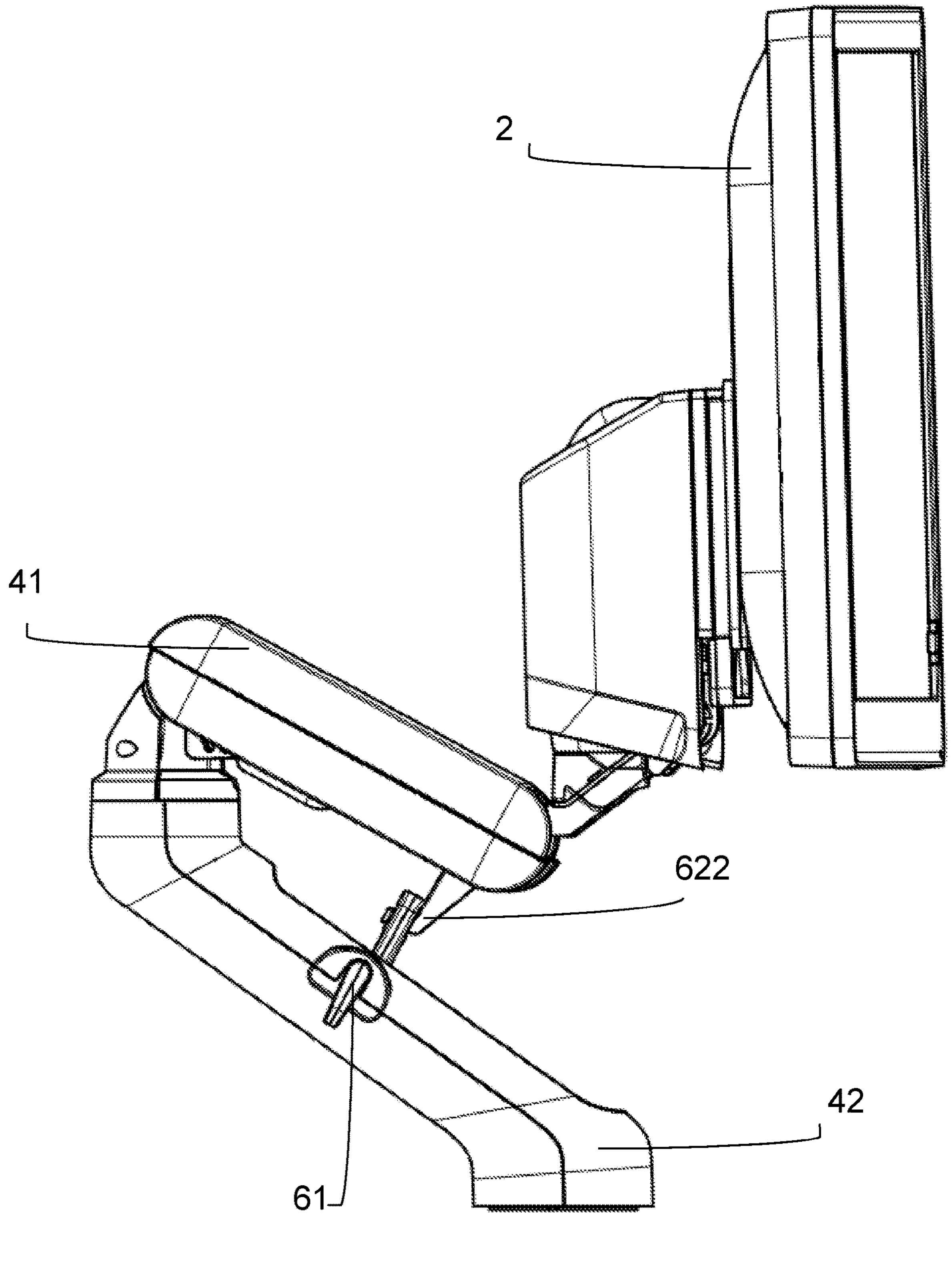
FIG. 11 is a perspective view of an articulating arm assembly according to a further embodiment where the component having a protrusion is in the upper arm and the lever in the lower arm in the locked state.

In the embodiment shown in FIG. 10*a*, FIG. 10*b* and FIG. 11, the articulating arm is again composed by an upper arm 41, a lower arm 42 and a joint 43, forming together kinematically a pantograph. The lower arm 42 is mounted on the control panel 3 and can rotate relative to it around the vertical axis through a rotating shaft; the upper arm 41 can rotate left and right and up and down relative to the lower arm 42 due to the joint 43, while the display 2 can rotate left and right and up and down relative to the upper arm 41 (in FIG. 10*b*, the vertical rotation axis is represented by a dashed line and the allowed movements are represented by arrows). In this embodiment the lever 61 is placed in the lower arm 42 and the component 62 is placed in the upper arm 41, forming an arm-to-arm lock due to the geometric interference between the draft of the protrusion 622 and the hole 612 placed in the lever 61. Magnets can be added to help the keeping of the lever 61 in the desired state also in this configuration.

Figure 12:
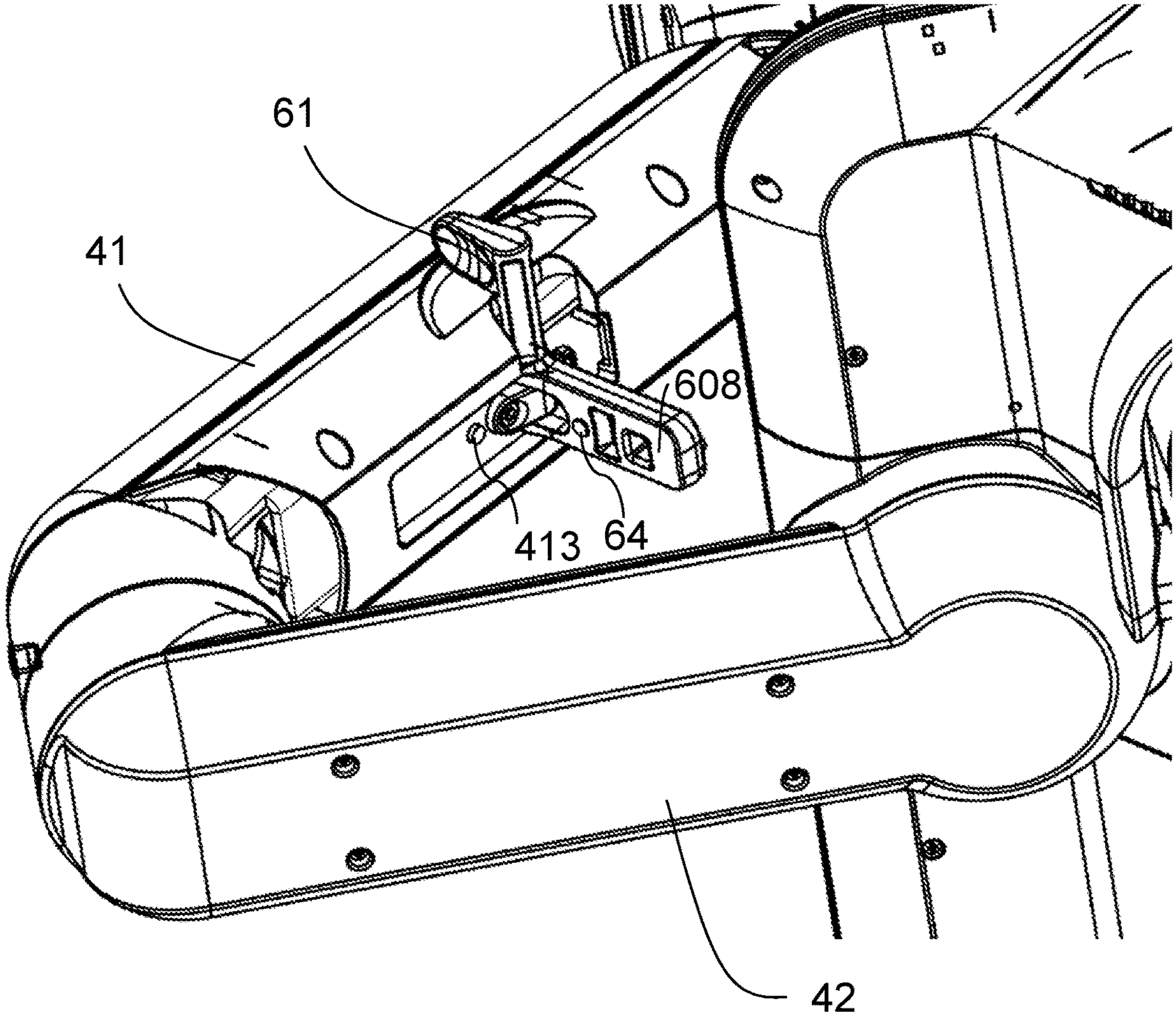
FIG. 12 is a perspective view of an articulating arm assembly according to another embodiment where the rest position is kept thanks to the attraction force between a magnet in the lever and a screw in the recess in the plastic cover.

FIG. 12 shows another embodiment where the rest position is kept due to the attraction force between the magnet 64 in the lever 61 and a second screw 413 in the recess in the plastic cover 411. This solution allows the use of the lock device of example embodiments of the present invention when the internal structure is not realized in a metallic material or when it's necessary that the internal structure is not exposed to the external environment and therefore the plastic cover cannot be holed.

Figure 13:
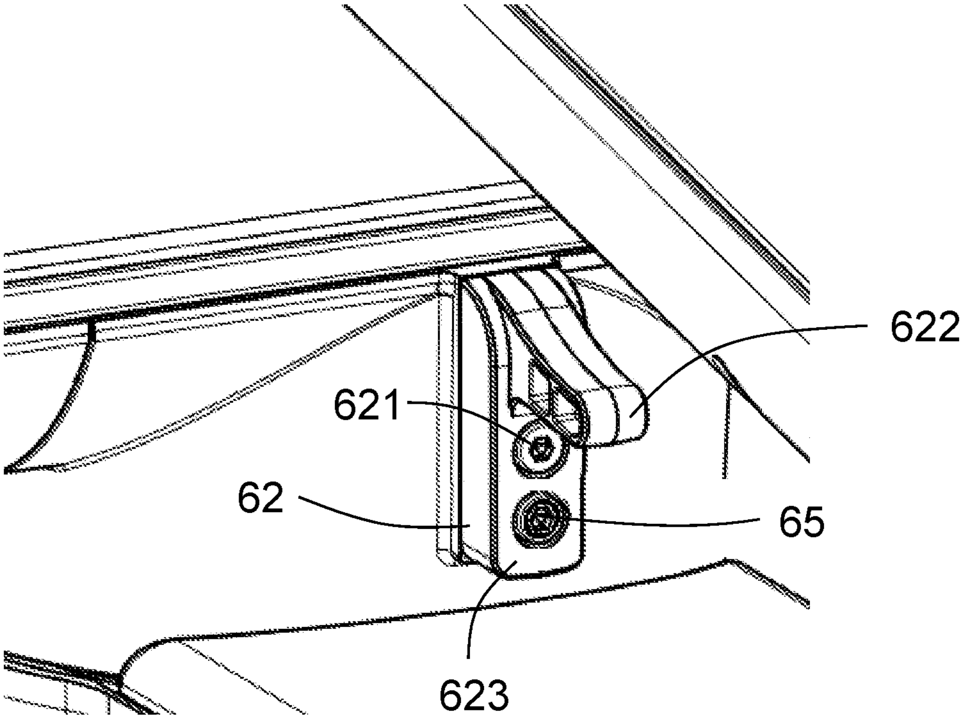
FIG. 13 is a detailed view of the component having a protrusion according to a further embodiment where a hook-and-loop fasteners tape is used.

FIG. 13 shows an embodiment where the component 62 has a piece of hook-and-loop fasteners 65 (in this case there is the counterpart in the lever) to help the keeping of the lever 61 in the locked state. Similarly, the keeping in the rest state can be assisted by the coupling of counterparts of hook-and-loop fasteners in the lever 61 and in the plastic cover 411 of the upper arm 41.

Figure 14:
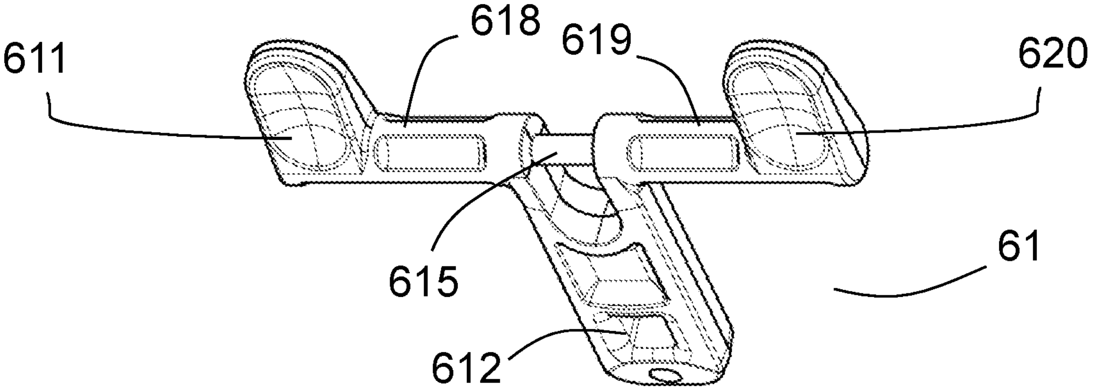
FIG. 14 is a perspective view of a lever according to a further embodiment where there is a double grip on the lever.

In the embodiment shown in FIG. 14, the locking rod 61 has a double grip (611 and 620) to be equally comfortable for left and right handed users: during the locking phase right handed user would find comfortable to use the grip 611 with the right hand while the left hand is used to lower the upper arm 41; on the opposite, left handed user would find comfortable to use the grip 620 at the end of prolongation 619 of the cylinder portion 615 with the left hand while the right hand is used to lower the upper arm 41.

Figure 15:
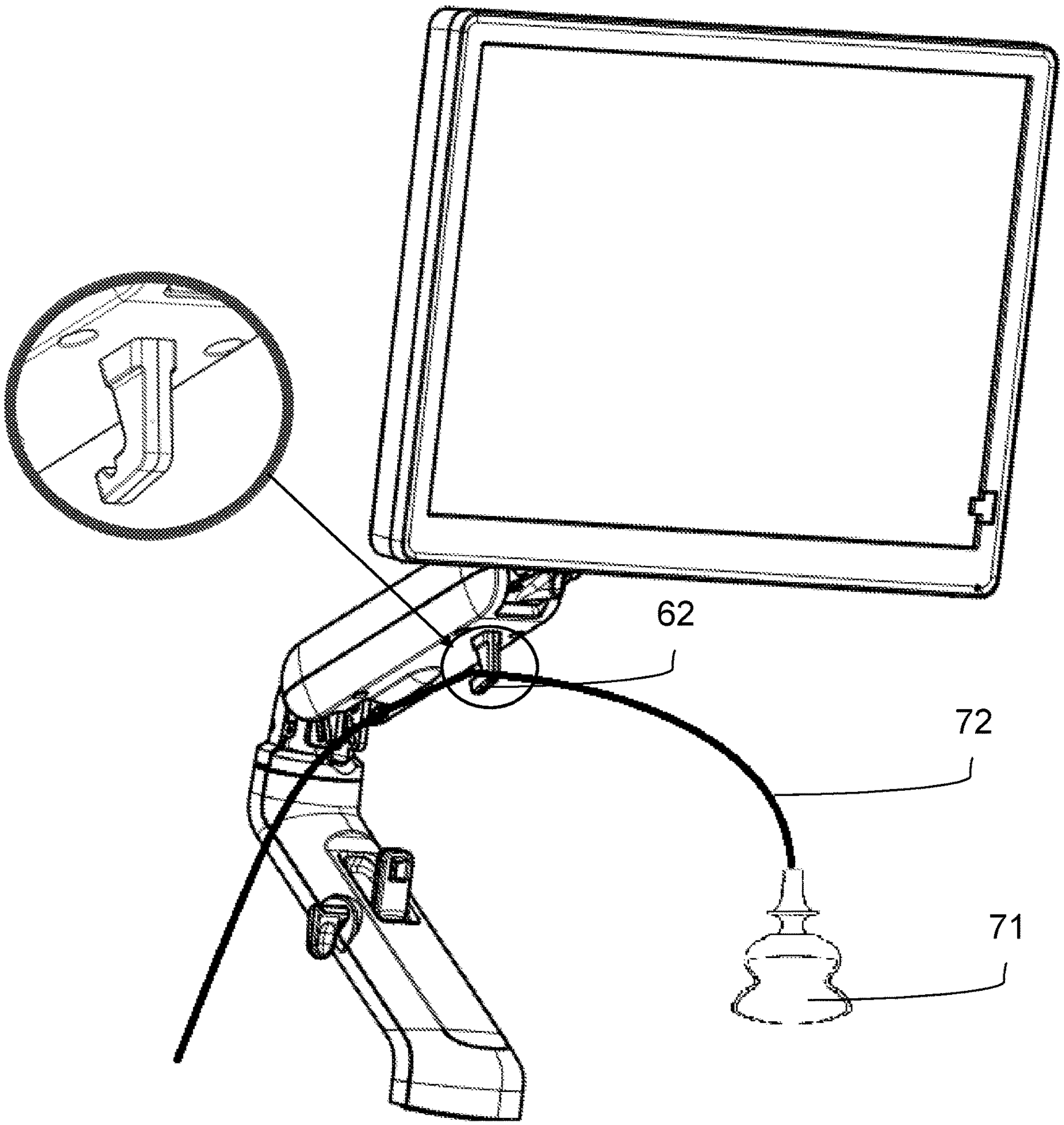
FIG. 15 is a perspective view of the articulating arm of FIG. 10*a* according to a further embodiment where the element having a protrusion is used as cable holder when the lever is in the rest position.

In the embodiment shown in FIG. 15, the protrusion 622 of component 62 is used, in the unlocked state, as a support for the cable 72 of a probe 71. The seat for the cable can be realized directly by moulding, without additional afterwards processing. In this way, becoming a multipurpose tool, the invention results more efficient than the prior art, according to another aspect.

Although mainly disclosed as connecting the flat panel display to the control panel or the main body, the skilled person would understand that the articulating arm assembly according to the invention can also be used to connect the control panel to the main body with any type of locking mechanism.

Two articulating arm assemblies may also be present to support both the flat panel display and the control panel. One or both the articulating arm assemblies may be associated to any of the locking mechanisms disclosed above, also of different type in the same system.

Figure 16:
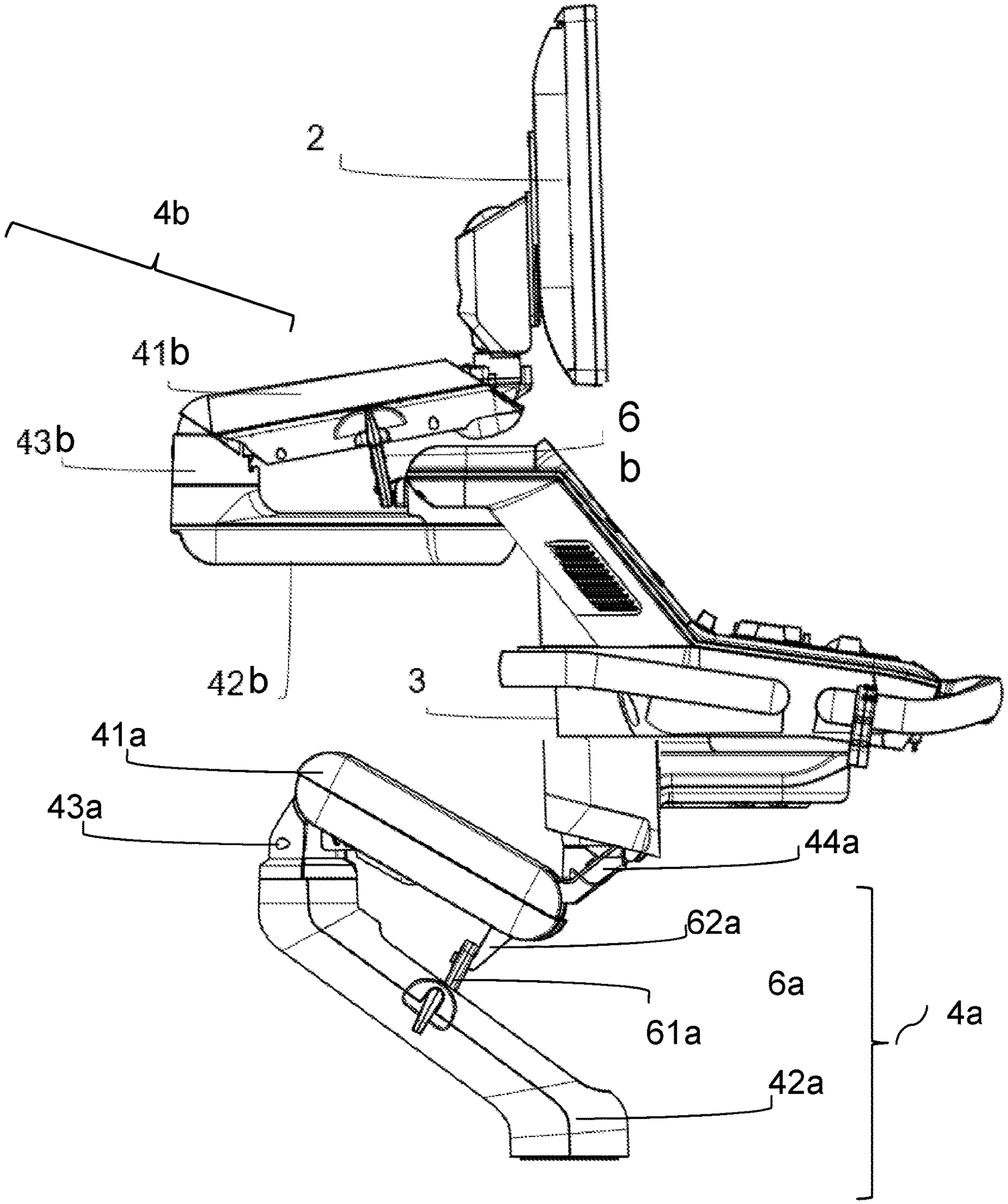
FIG. 16 shows the upper group of an ultrasound apparatus according to another embodiment in which the locking device is applied on an articulating arm that supports a control panel.

According to the embodiment shown in FIG. 16, the locking device 6*a* is applied on an articulating arm 4*a* that supports the control panel 3. The lower am 42*a* is mounted on the main body of the apparatus 5 (not shown) and can rotate around a vertical axis through a rotating shaft. The upper arm 41*a* can rotate left and right and up and down through the joint 43*a* (that connects the two arms) and the control panel 3 can rotate left and right through the joint 44*a* that connects It with the upper arm 41*a*. The locking device 6*a* shown in the figure is the arm-to-arm lock described in FIGS. 10 to 11, with the component 62*a* mounted in the upper arm 41*a* and the lever 61*a* hinged to the lower arm 42*a*, but alternately it can be used the first lock (FIGS. 2 to 9) with the lever 61 on the upper arm 41 and the component 62 mounted on an appropriate space on the main body 5. In both configurations the display 2 can be supported by a simpler arm (that can only rotate left and right and enable the up and down of the monitor 2) or can be supported, as shown in the figure, by a second articulating arm 4*b*, comprising an upper arm 41*b*, a second lower arm 42*b*, the joints 43*b* and 44*b*, whose functioning has been previously illustrated, and an optional second lock device 6*b*.

The system according to embodiments herein represents an improvement over the known systems as It is simpler, it is safer, avoiding spring restoring forces and being easy to clean, it uses a minor number of parts, so it is consequently cheaper, more compact and more reliable (fewer parts equal less probability of breakage or malfunctions), it requires a minor mass to be moved and consequently it requires less effort to end user, and it can be used both for displays and control panels as supported devices.

The above-presented description and figures are intended by way of example only and are not intended to limit the illustrative embodiments in any way except as set forth in the following claims. It is particularly noted that persons skilled in the art can readily combine the various technical aspects of the various elements of the various illustrative embodiments that have been described above in numerous other ways, all of which are considered to be within the scope of the claims.

The invention claimed is:

1. An ultrasonic diagnostic imaging system including a main body housing imaging electronics and a control panel coupled to the imaging electronics comprising:

a flat panel display electrically coupled to the imaging electronics;

an articulating arm assembly to which the flat panel display is connected for adjusting the viewing position of the flat panel display, or the control panel is connected for adjusting the position of the control panel, the articulating arm assembly including a first lower arm movably mounted to the main body or to the control panel and a second upper arm movably connected to the first lower arm and to the flat panel display, or the control panel, wherein at least one of the arms includes a 4-bar linkage; and a locking mechanism which acts to restrict motion of the articulating arm assembly, wherein the locking mechanism comprises a protrusion and a lever having a corresponding seat for engagement of the protrusion, the lever being hinged on one of the two arms to pivot from a rest position to a lock position, the protrusion being correspondingly located on the other arm or the control panel or the main body or a support thereof to engage the seat of the lever when the lever is in the lock position, the rest position being a non-interfering position whereby the lever is substantially contained in a recess, the locked position being a position whereby at least part of the lever extends further beyond the recess than when in the rest position.

2. The system according to claim 1, wherein the recess is located in a plastic cover of the arm to which the lever is hinged and has a shape complementary to the shape of the lever so that such arm can expose an external even surface when the locking mechanism is in the rest position.

3. The system according to claim 1, wherein the lever has a shape having a first and a second opposing flat surfaces, wherein the first surface is adapted to contact the arm to which the lever is hinged when the lever is in rest position while the second surface is adapted to contact the protrusion or a support thereof when the lever is in lock position.

4. The system according to claim 1, wherein the lever is maintained in the lock position by an attraction force acting between a first element associated with the lever and an element associated with the protrusion or a support thereof.

5. The system according to claim 4, wherein the first element associated with the lever is associated with the second surface of the lever.

6. An ultrasonic diagnostic imaging system including a main body housing imaging electronics and a control panel coupled to the imaging electronics comprising:

a flat panel display electrically coupled to the imaging electronics;

an articulating arm assembly to which the flat panel display is connected for adjusting the viewing position of the flat panel display, or the control panel is connected for adjusting the position of the control panel, the articulating arm assembly including a first lower arm movably mounted to the main body or to the control panel and a second upper arm movably connected to the first lower arm and to the flat panel display, or the control panel, wherein at least one of the arms includes a 4-bar linkage; and a locking mechanism which acts to restrict motion of the articulating arm assembly, wherein the locking mechanism comprises a protrusion and a lever having a corresponding seat for engagement of the protrusion, the lever being hinged on one of the two arms to pivot from a rest position to a lock position, the protrusion being correspondingly located on the other arm or the control panel or the main body or a support thereof to engage the seat of the lever when the lever is in the lock position, the rest position being a non-interfering position whereby the lever is substantially contained in a recess;

wherein the lever is maintained in the lock position by an attraction force acting between a first element associated with the lever and an element associated with the protrusion or a support thereof;

wherein the element associated with the protrusion is a metallic element, like the head of a screw; fixed to the protrusion or to a support thereof, while the first element associated with the lever is a magnet fixed to the lever or a support thereof or vice versa.

7. The system according to claim 4, wherein the element associated with the protrusion and the first element associated with the lever comprise corresponding parts of a fastening device of the hook-and-loop type.

8. An ultrasonic diagnostic imaging system including a main body housing imaging electronics and a control panel coupled to the imaging electronics comprising:

a flat panel display electrically coupled to the imaging electronics;

an articulating arm assembly to which the flat panel display is connected for adjusting the viewing position of the flat panel display, or the control panel is connected for adjusting the position of the control panel, the articulating arm assembly including a first lower arm movably mounted to the main body or to the control panel and a second upper arm movably connected to the first lower arm and to the flat panel display, or the control panel, wherein at least one of the arms includes a 4-bar linkage; and a locking mechanism which acts to restrict motion of the articulating arm assembly, wherein the locking mechanism comprises a protrusion and a lever having a corresponding seat for engagement of the protrusion, the lever being hinged on one of the two arms to pivot from a rest position to a lock position, the protrusion being correspondingly located on the other arm or the control panel or the main body or a support thereof to engage the seat of the lever when the lever is in the lock position, the rest position being a non-interfering position whereby the lever is substantially contained in a recess;

wherein the lever comprises a second element configured to exert a magnetic force on the metallic body of the arm to which the lever is hinged, or on a metallic element, like the head of a screw; associated with such arm, when the lever is in rest position.

9. The system according to claim 8, wherein the second element is associated with the first surface of the lever.

10. An ultrasonic diagnostic imaging system including a main body housing imaging electronics and a control panel coupled to the imaging electronics comprising:

a flat panel display electrically coupled to the imaging electronics;

an articulating arm assembly to which the flat panel display is connected for adjusting the viewing position of the flat panel display, or the control panel is connected for adjusting the position of the control panel, the articulating arm assembly including a first lower arm movably mounted to the main body or to the control panel and a second upper arm movably connected to the first lower arm and to the flat panel display, or the control panel, wherein at least one of the arms includes a 4-bar linkage; and a locking mechanism which acts to restrict motion of the articulating arm assembly, wherein the locking mechanism comprises a protrusion and a lever having a corresponding seat for engagement of the protrusion, the lever being hinged on one of the two arms to pivot from a rest position to a lock position, the protrusion being correspondingly located on the other arm or the control panel or the main body or a support thereof to engage the seat of the lever when the lever is in the lock position, the rest position being a non-interfering position whereby the lever is substantially contained in a recess;

wherein the lever has a slit in the end portion hosting a transversal cylindrical portion acting as a pivot axis.

11. The system according to claim 10, further comprising a prolongation of the cylindrical portion on one side of the lever ending with a gripping appendix substantially coplanar with the lever and extending in the opposite direction of the lever so that when the appendix is rotated in one direction around the pivot axis the lever rigidly rotates in the same direction.

12. The system according to claim 11, further comprising a prolongation of the cylindrical portion also on the opposite side of the lever and ending with a further gripping appendix so that the lever can be indistinctly rotated acting on either side.

13. The system according to claim 1, wherein the lever is hinged to the second arm while the protrusion is associated with the control panel or the main body or a support thereof or the lever is hinged to the first arm while the protrusion is associated with the second arm.

14. The system according to claim 1, wherein the protrusion is an elongated element extending from a support block fixed, or to be fixed, to the control panel or the main body, such block having a flat surface adapted to contact the second surface of the lever when in lock position, the attraction element associated with the protrusion being located on such flat surface.

15. The system according to claim 14, wherein the attraction element is the head of a screw fixing the support block to the control panel or the main body.

16. The system according to claim 1, wherein the protrusion has the shape of a hook for holding the probe cable when the lever is in rest position.

17. An ultrasonic diagnostic imaging system including a main body housing imaging electronics and a control panel coupled to the imaging electronics comprising:

a flat panel display electrically coupled to the imaging electronics;

an articulating arm assembly to which the flat panel display is connected for adjusting the viewing position of the flat panel display, or the control panel is connected for adjusting the position of the control panel, the articulating arm assembly including a first lower arm movably mounted to the main body or to the control panel and a second upper arm movably connected to the first lower arm and to the flat panel display, or the control panel, wherein at least one of the arms includes a 4-bar linkage;

a locking mechanism which acts to restrict motion of the articulating arm assembly, wherein the locking mechanism comprises a protrusion and a lever having a corresponding seat for engagement of the protrusion, the lever being hinged on one of the two arms to pivot from a rest position to a lock position, the protrusion being correspondingly located on the other arm or the control panel or the main body or a support thereof to engage the seat of the lever when the lever is in the lock position, the rest position being a non-interfering position whereby the lever is substantially contained in a recess; and an additional articulating arm assembly to which the control panel, or the flat panel display, is connected, the additional articulating arm assembly including an additional first lower arm movably mounted to the main body or the control panel and an additional second upper arm movably connected to the additional first lower arm and to the control panel, or the flat panel display, and an additional locking mechanism which acts to restrict motion of the additional articulating arm assembly, wherein the additional locking mechanism comprises an additional protrusion and an additional lever having a corresponding additional seat for engagement of the additional protrusion, the additional lever being hinged on one of the additional two arms to pivot from a rest position to a lock position, the additional protrusion being correspondingly located on the other additional arm or the main body or the control panel or a support thereof to engage the additional seat of the additional lever when the additional lever is in the lock position, the rest position being a non-interfering position whereby the additional lever is substantially contained in a recess.

* * * * *